United States Patent [19]

Terwilliger

[11] Patent Number: 5,183,052
[45] Date of Patent: Feb. 2, 1993

[54] AUTOMATIC BIOPSY INSTRUMENT WITH CUTTING CANNULA

[76] Inventor: Richard A. Terwilliger, 1489 Cas Vallecita, Alamo, Calif. 94507

[21] Appl. No.: 610,006

[22] Filed: Nov. 7, 1990

[51] Int. Cl.⁵ .............................................. A61B 10/00
[52] U.S. Cl. ................................... 128/753; 128/754; 606/170
[58] Field of Search ............... 128/753, 752, 754, 751, 128/755, 749, 750, 760, 763, 765, 770; 606/167, 170, 181, 182, 184, 185

[56] References Cited

U.S. PATENT DOCUMENTS

| | | | |
|---|---|---|---|
| 4,476,864 | 10/1984 | Tezel | 128/754 |
| 4,570,632 | 2/1986 | Woods | 128/751 |
| 4,600,014 | 7/1986 | Beraha | 128/754 |
| 4,699,154 | 10/1987 | Lindgren | 128/754 |
| 4,747,414 | 5/1988 | Brossel | 128/754 |
| 5,025,797 | 6/1991 | Baran | 128/754 |

FOREIGN PATENT DOCUMENTS

| | | |
|---|---|---|
| 10321 | 10/1979 | European Pat. Off. . |
| 1160573 | 1/1964 | Fed. Rep. of Germany ...... 128/754 |
| 141108 | 4/1980 | German Democratic Rep. . |
| 83/03313 | 10/1983 | PCT Int'l Appl. . |
| 1551362 | 3/1990 | U.S.S.R. ............................... 128/754 |

OTHER PUBLICATIONS

Brun Del Re et al. English translation of German patent EP 10321.

Primary Examiner—Max Hindenburg
Assistant Examiner—Guy V. Tucker
Attorney, Agent, or Firm—Fliesler, Dubb, Meyer & Lovejoy

[57] ABSTRACT

An automatic biopsy instrument includes a cannula 13 provided over a stylet 11. The stylet 11 directs the cannular 13 to a biopsy site. The instrument urges the cannula 13 past the stylet 11 in order to collect a tissue sample and simultaneously causes a vacuum to be communicated to said cannular 13 in order to assist the collection of the tissue sample by the cannula 13.

18 Claims, 5 Drawing Sheets

AUTOMATIC BIOPSY INSTRUMENT WITH CUTTING CANNULA

FIELD OF THE INVENTION

This invention relates to an automated mechanism for collecting a tissue sample from humans or animals by a procedure referred to as tissue biopsy, and more particularly to an instrument for automatically performing the tissue extraction from a tissue mass in a precise and rapid manner with minimum patient discomfort.

BACKGROUND OF THE INVENTION

It is often desirable and frequently absolutely necessary to sample or test a portion of tissue from humans and even animals to aid in the diagnosis and treatment of patients with cancerous tumors, pre-malignant conditions and other diseases or disorders. Tumors are first noted in a patient by one of three ways, palpation, X-ray imaging or ultrasound imaging. Typically, in the case of cancer or the suspicion of malignant tumors, a very important process called tissue biopsy is performed to establish whether cells are cancerous.

Biopsy may be done by an open or closed technique. Open biopsy removes the entire tissue mass or a part of the tissue mass. Closed biopsy on the other hand is usually performed with a needle-like instrument and may be either an aspiration biopsy (hollow needle on a syringe) or a cored biopsy (special tissue cutting needle design). In needle aspiration biopsy, individual cells or clusters of cells are obtained for cytologic examination. In core biopsy, a segment of tissue is obtained for histologic examination which may be done as a frozen section or paraffin section.

The methods and procedures of obtaining tissue samples for cytologic or histologic examination have been performed historically by manual insertion and manipulation of the needle. These procedures are performed blind by the physician and guided by feel and known anatomic landmarks.

One prior art manual biopsy device includes a syringe arrangement including a stylet surrounded by a cannula. The stylet has a pointed tip and behind the tip a reduced diameter shank. The diameter of the pointed tip is slightly less than the internal diameter of the cannula such that the tip prevents tissue from entering the cannula as the cannula is passed through surrounding tissue to the point of intended biopsy. An O-ring is placed in sealing relationship between the reduced diameter shank and the internal diameter of the cannula. During operation of the biopsy syringe, the cannula is urged forward past the tip of the stylet in order to collect a tissue sample. As this occurs, a vacuum is formed in the cannula between the O-ring and the tissue sample. This vacuum tends to draw the tissue sample into the cannula.

This device, however, has disadvantages in that it is manual and thus does not give totally reliable results, as discussed below, in taking a biopsy of a very small tumor. Further, the vacuum created would be somewhat limited do the size of the cannula.

Examples of tissue harvesting devices have been described in U.S. Pat. Nos. 4,651,752; 4,702,260; and 4,243,048.

Two very important innovations in medical technology have influenced the field of tissue biopsy in the last five years. One is the use of tissue imaging devices which allow the physician to see inside the body and visually guide the needle to the tumor mass. The second is the invention of the Automatic Core Biopsy Device (ACBD). The ACBD is an instrument which propels a needle set with considerable force and speed in order to pierce the tumor mass and collect the tissue sample. This ACBD has allowed physicians to test tissue masses in the early stages of growth and has contributed to the medical trend of early diagnosis and successful treatment of cancer.

The Automated Core Biopsy Device allows a biopsy to be performed on tumor masses as small as two millimeters in diameter. This procedure is performed under ultrasound or X-ray guidance. Tumors of this size cannot be biopsied reliably by hand since the tumor is about the same size as the biopsy needle. Manual attempts at biopsy pushes the tumor away without piercing the mass. Automatic puncture devices accelerate the needle at such a velocity that even a small tumor can be pierced.

Automated Core Biopsy Devices (ACBD) use the True Cut needle set design. The True Cut needle is comprised of an inner notched stylet with an outer cannula. The stylet is advanced into the tissue under spring power followed by the cannula which cuts and traps the tissue sample in the notch of the stylet. The True Cut needle yields a core sample which is semi-circular in cross-section with a length determined by the stroke of the ACBD.

The stylet is a needle with a notched cut-out at the distal end. The cannula is a hollow needle with an angled cutting surface at the distal end which slides over the stylet. When the stylet is pushed into the tissue, the tissue is pierced and relaxes into the notched cut-out. When the cannula is slid forward, the tissue in the notch of the stylet is sliced off and retained in the notch until the cannula is drawn back.

The most common True Cut needle size used by ACBD's is 18 gage. The use of 18 gage needles is a compromise between the physician's desire to use the smallest, least invasive, needle gage and the pathologist's needs for as large a tissue sample as possible to minimize false-positive diagnosis. This compromise in needle size leads the physician to obtain multiple core samples from the biopsy site to allow the pathologist sufficient tissue for an accurate diagnosis.

The requirements of the physician and the pathologist dictate the need for an alternative approach in the function and design of the conventional ACBD and needle sets. The ideal product would allow the use of smaller needle gages and/or lessen the need for multiple samples to be taken from a given biopsy site.

SUMMARY OF THE INVENTION

Based on the prior art instruments for biopsy sampling of tissue masses and the actual present state of this art, there exists a need for an instrument which is capable of obtaining biopsy samples which yield more tissue volume for a given needle gage than currently marketed devices. This increased tissue volume allows the physician to use smaller needle gages and/or reduce the number of punctures per biopsy site.

The ability to use smaller needle gages and/or less punctures per biopsy site, opens up the other major areas of biopsy procedures to the use of a device which will increase the reliability and safety of these procedures.

Accordingly, I have invented an instrument for removing cylindrically shaped tissue samples of pre-determined size from a tissue mass with an instrument that automatically penetrates, captures and removes the tissue sample for examination.

The instrument is a spring powered mechanical design. The needle set is integral with the housing and consists of a outer hollow cannula and an inner pointed tipped stylet. The stylet is stationary and the cannula is driven forward under spring force.

In a preferred embodiment, the housing is comprised of a cavity which guides a spring backed piston to which the cannula is attached. Once the spring is released, the piston and cannula are driven forward. As the piston advances, a vacuum is created behind the piston, with the only outlet for this vacuum being down the bore of the advancing cannula. As the tissue is penetrated by the cannula, a vacuum force is exerted on the captured tissue and this vacuum force pulls the tissue down the bore of the cannula. The vacuum holds the tissue and allows the tissue to break off at the tip of the distal end as the needle is withdrawn.

The stylet is a stationary needle which has a reduced diameter beyond the distal pointed tip to allow for the creation of the maximum vacuum force in the piston and cannula. At the distal end of the stylet, a solid pointed tip facilitates the introduction of the needles into the tissue mass. The stylet is positioned flush with the end of the cannula in the cocked position. In the cocked position, the stylet prevents tissue from entering the cannula as the needle set is introduced into the body. As the device is fired, the cannula advances while the stylet remains stationary, thus allowing space for the penetrated tissue to enter the cannula.

As the device is cocked and the piston and cannula are retracted, the cannula is moved backwards over the stationary stylet, pushing the tissue sample out of the cannula. This action removes the tissue sample and cocks the gun in one motion.

A volumetric analysis of a cross-section of tissue area collected with the True Cut needle set vs. the cylindrical core samples of this invention follows:

| Stylet | Gage | X-Section Area | Percentage |
|---|---|---|---|
| True Cut | 18 ga. | .0007 sq/in. | |
| Cylindrical | 18 ga. | .0012 sq/in. | 72% larger sample |
| Cylindrical | 20 ga. | .0005 sq/in. | 71% of True Cut 18 ga. |

For a given needle gage and core length, the cylindrical core volume of this invention is 72% larger than that provided by the True Cut needle set. A 20 gage cylindrical needle in accordance with this invention will yield 71% of the tissue yielded by an 18 gage True Cut needle set.

Accordingly, it is a principle object of this invention to provide an automated tissue sampling device for obtaining tissue samples which have a circular cross-section. Such a cross-section provides for more tissue mass for a given needle gage, provides for a less invasive procedure with reduced tissue trauma and allows for the maximum tissue to be harvested with the minimum number of samples taken.

It is a further object of this invention to provide a biopsy instrument which accelerates a needle at such a velocity so as to allow penetration of small tissue masses that would otherwise be too small for a closed biopsy procedure.

It is another object of this invention to provide an instrument which may be used to obtain multiple tissue samples from the same biopsy site without disassembling the device or actuating multiple mechanisms or controls.

It is yet another object of the invention to provide an automated biopsy device which creates a vacuum substantial enough to effectively assist in drawing and holding the tissue in the cannula so that as the cannula is withdrawn, the tissue sample breaks off from the tissue mass being biopsied.

These and other objects of the invention will be apparent from the following descriptions and claims.

BRIEF DESCRIPTION OF THE DRAWINGS

The above noted advantages and other characteristic features of the present invention will be apparent from the accompanying drawings, and in part pointed out in the following detailed description of the preferred embodiment of the invention in which references will be made to the accompanying drawings wherein like reference numerals designate corresponding parts and wherein.

DESCRIPTION OF THE PREFERRED EMBODIMENT

Figure 1A:
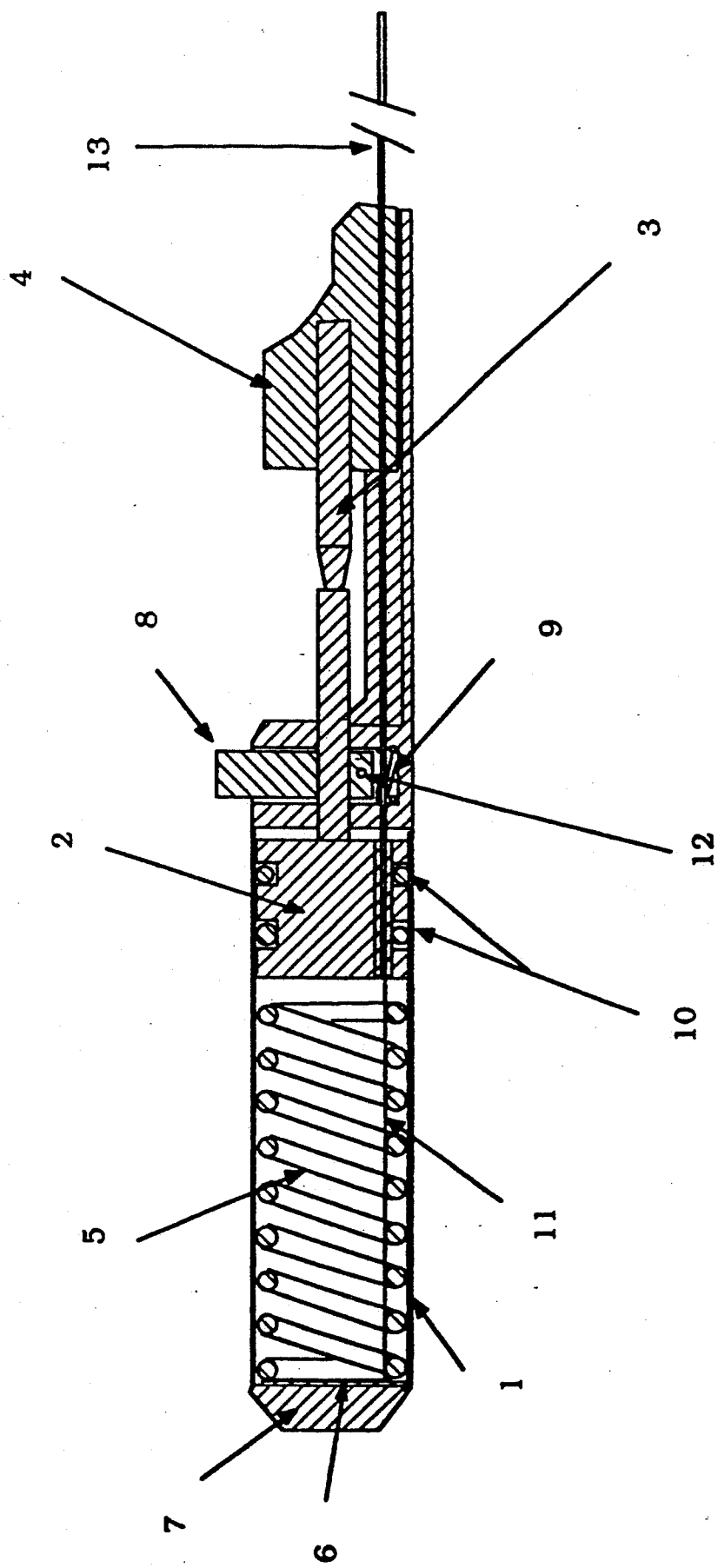
FIG. 1A and 1B are side elevation views of the biopsy instrument of this invention in uncocked and cocked positions, respectively.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Considering now the drawings in detail, FIG. 1A illustrates a side elevation view of the embodiment of the inventive biopsy instrument which is shown to depict the main components of said embodiment with the main body shown generally at 1 and the tissue piercing and removal device, cannula 13. The main housing 1 extends from end cap 7 to the thumb knob 4. Within said housing 1 is a plunger 2 with annular grooves that capture two "O"-rings seals 10.

Plunger rod 2 is depressed by exerting pressure on thumb knob 4 which compresses the main spring 5. Plunger 2 and main spring 5 are held in the compressed state by latch pin 12 which resides on actuator button 8

Figure 1B:
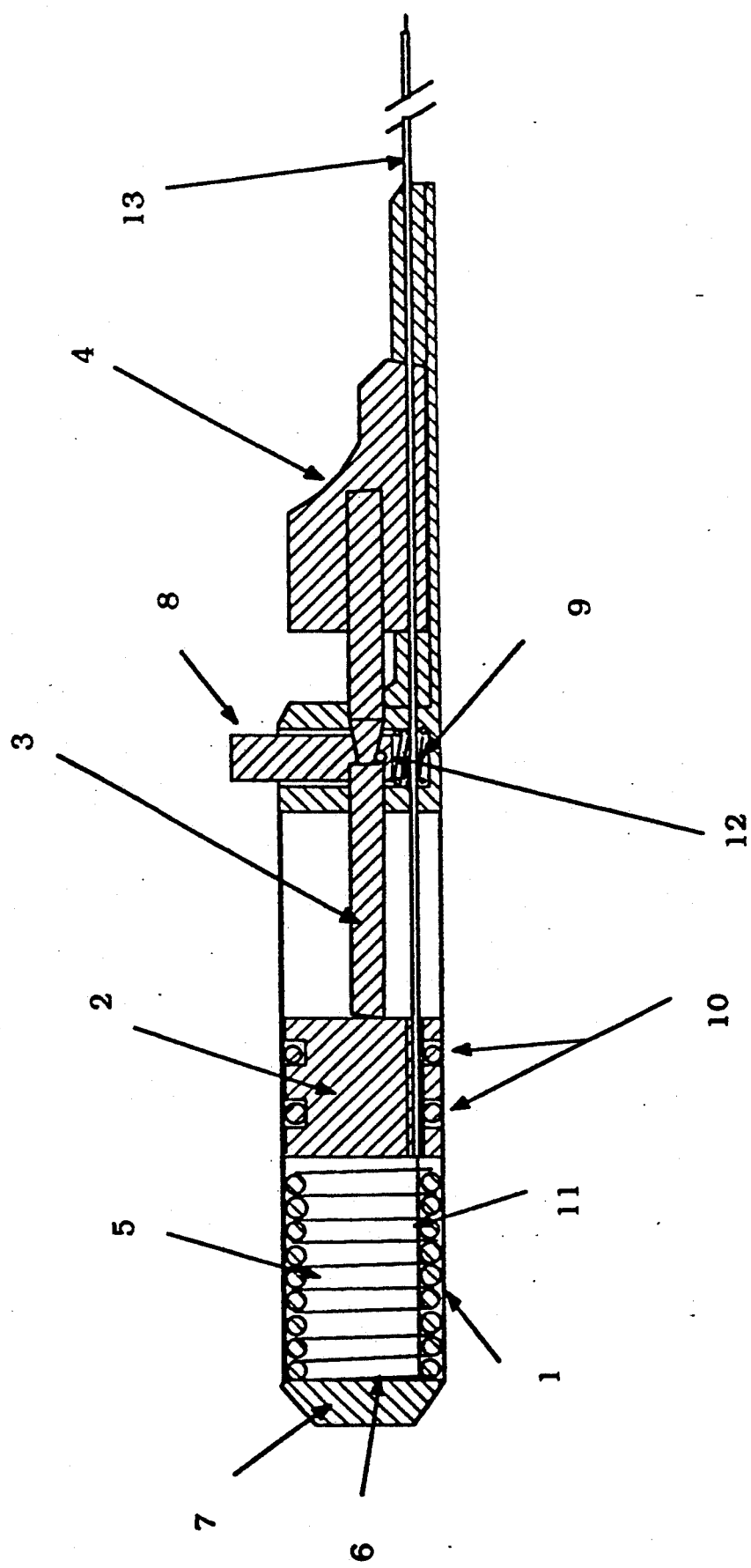

(FIG. 1B). Spring 9 pushes actuator button 8 and latch pin 12 up against plunger rod 3. As plunger rod 3 is depressed latch pin 12 slides along plunger rod 3 until latch pin 12 detents into the annular groove in plunger rod 3. Latch pin 12 holds plunger rod 3 in place and thus holds plunger 2 and main spring 5 in compression until such time that actuator button 8 is depressed releasing plunger rod 3. As plunger rod 3 is released, main spring 5 pushes plunger 2 forward with the associated component cannula 13 which is attached to plunger 2.

Cannula 13 is fixed to plunger 2 through a hole in plunger 2 and sealed such that plunger 2 with the associated "O"-rings 10 and end cap 7 with associated "O"-ring 6 create an air tight chamber or cavity in main housing 1 between the end cap 7 and the plunger 2, with the hollow body of cannula 13 the only avenue of air passage.

Figure 2:
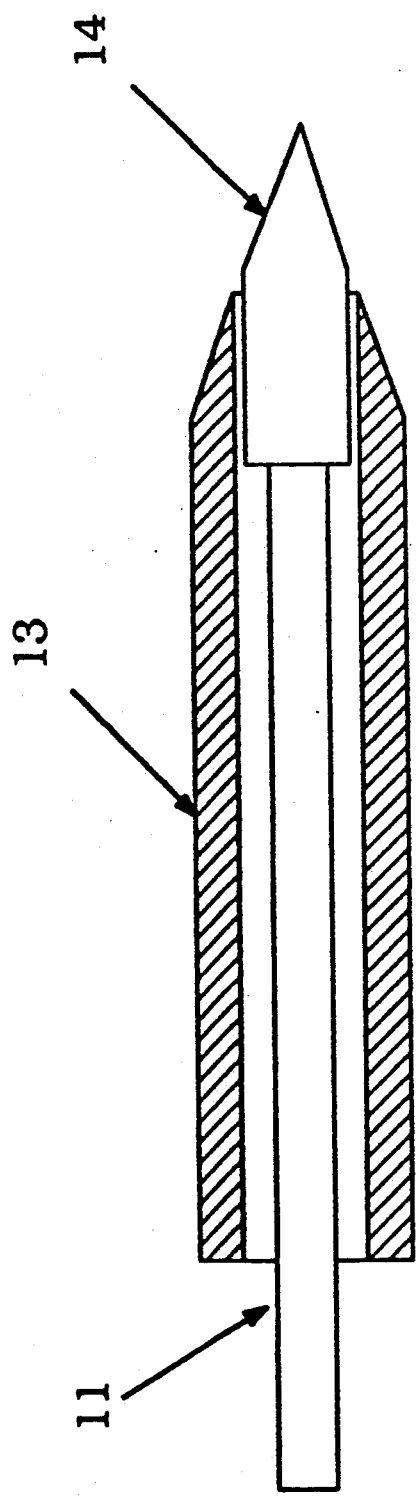
FIG. 2 is a partial side elevation of a stylet and a cannula of the biopsy instrument in FIGS. 1A and 1B in a cocked position.

When thumb knob 4 is depressed and plunger rod 3 compresses main spring 5, air is evacuated through cannula 13. Depressing actuator button 8 releases plunger rod 3 thus allowing plunger 2 to be forced forward by main spring 5 (FIG. 1B). As plunger 2 moves forward a vacuum is created in the main housing 1 between end cap 7 and the advancing plunger 2. The outer diameter of the tip 14 of the stylet 11 is of substantially the same diameter as the diameter of the bore of the cannula 13 so as to prevent tissue from entering the cannula 13 as the instrument is advanced through the tissue. The diameter of the tip 14 of the stylet 11 is, however, small enough relative to the bore diameter to allow the passage of air between the inner diameter of the cannula 13 and the outer diameter of the tip 14 of the stylet 11 (FIG. 2). As cannula 13 is thrust forward by plunger 2, the vacuum in main housing 1 creates a suction force down the bore of cannula 13. Stylet 11 extends down the bore of cannula 13 and is attached to main housing 1 at the point where end cap 7 is attached. Stylet 11 remains stationary in respect to main housing 1 as cannula 13 slides over stylet 11 and pierces the tissue. The reduced diameter shank of stylet 11 allows the suction generated in main housing 1 to provide maximum effect on pierced tissue captured in cannula 13. The captured tissue in cannula 13 acts as a seal thus maintaining a vacuum on the captive tissue in cannula 13 allowing the tissue to break off at the distal end of cannula 13 and be extracted from the tissue mass.

FIG. 2 illustrates a cross-sectional side elevation view of the distal ends of cannula 13 and stylet 11. Stylet 11 is a dual diameter solid rod with a pointed tip 14 at the distal end. Tip 14 prevents tissue from entering cannula 13 as cannula is passed through surrounding tissue to the point of intended biopsy.

Figure 3A:
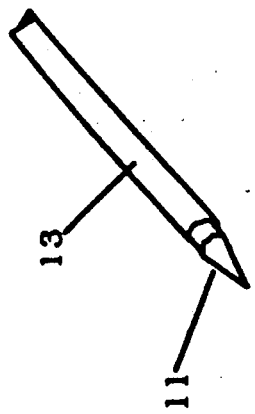
FIG. 3A, 3B, and 3C are pictorial illustrations of needle set positioned in various stages of the invention's operation.
Figure 3B:
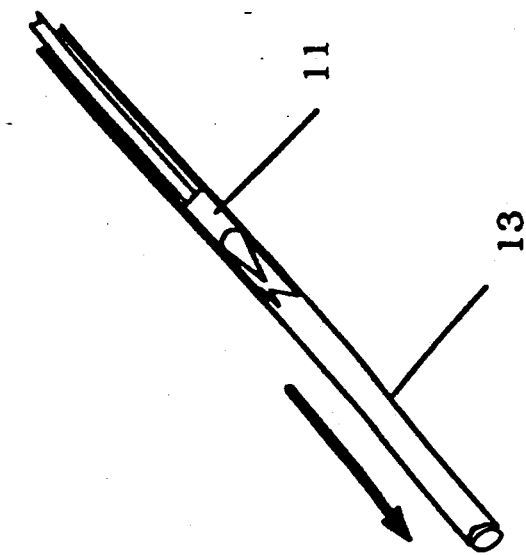
Figure 3C:
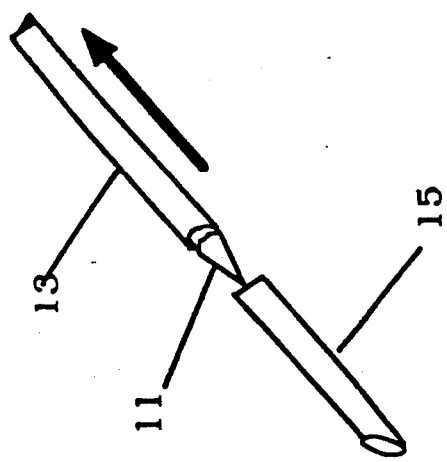

FIGS. 3A, 3B and 3C illustrate the preferred embodiment of the distal needle end of this invention. Three stages of motion are depicted. FIG. 3A shows cannula 13 and stylet 11 in the cocked position; FIG. 3B shows cannula 13 and stylet 11 in the fired position. FIG. 3C shows cannula 13 and stylet 11 in the act of cocking the mechanism and the subsequent expulsion of the tissue sample.

FIGS. 4A, 4B, 5A and 5B illustrate a comparison of the tissue sample obtained at the distal needle ends of the preferred embodiment of this invention and tissue obtained by the True Cut needle design used in prior art biopsy instruments.

Figure 4A:
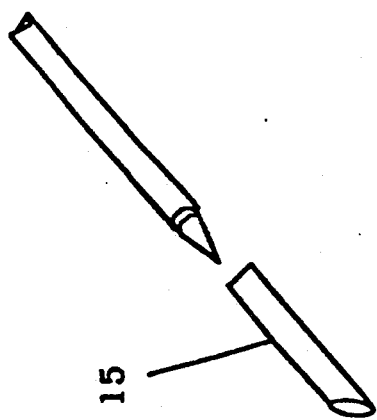
FIG. 4A is a pictorial illustration of the preferred embodiment of the distal needle end of the invention.

FIG. 4A illustrates the preferred embodiment of the distal needle end with the expulsed tissue sample 15.

Figure 4B:
FIG. 4B is a pictorial illustration of the cross-section of tissue obtained from the preferred embodiment of the invention.

FIG. 4B illustrates the cross-section of tissue 15 obtained from the distal end of the preferred embodiment of this invention.

Figure 5A:
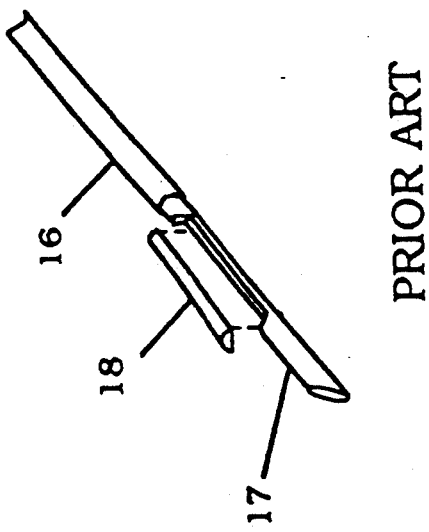
FIG. 5A is a pictorial illustration of the distal needle end of a prior art device.

FIG. 5A illustrates the distal needle end 17 extending from cannula 16 of the prior art device with the expulsed tissue sample 18.

Figure 5B:
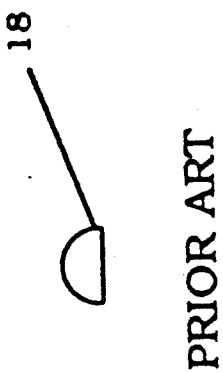
FIG. 5B is a pictorial illustration of the cross-section of tissue obtained from the prior art device of FIG. 5A.

FIG. 5B illustrates the cross-section of tissue 18 obtained from the distal needle end of the prior art device.

While the invention has been illustrated and described in detail in the drawings and foregoing description, the same is to be considered as illustrative and not restrictive in character, it being understood that only the preferred embodiment has been shown and described and that all changes and modifications that come within the spirit and scope of the invention are desired to be protected.

I claim:

1. An automatic biopsy instrument including:
  a body;
  a cavity defined in said body;
  a piston mounted in said cavity;
  means for biasing said piston relative to said cavity;
  means for urging said piston against the biasing means;
  an elongate cannula with an elongate inner bore;
  means for securing said cannula to said piston;
  means for communicating said inner bore of said cannula with the cavity of said body;
  a stylet positioned in said inner bore of said cannula; and
  said cannula being extended out beyond a tip of said stylet in response to said biasing means in order to create a tissue collection space.

2. The instrument of claim 1 wherein:
  said biasing means can bias said piston to an uncocked position;
  said urging means can urge said piston against said biasing means to a cocked position; and
  means for selectively locking said piston in said cocked position.

3. The instrument of claim 1 wherein:
  a volume defined by said cavity of said body is substantially larger than a volume defined by the inner bore of said cannula.

4. The instrument of claim 1 wherein:
  said stylet has a tip with a first diameter which is substantially the diameter of the bore of the cannula; and
  said stylet has a shank located behind said tip, which shank has a second diameter which is less than the first diameter of the tip and which second diameter extends from the tip substantially the length of the stylet.

5. An automatic biopsy instrument including:
  a body;
  a cavity defined in said body and having a proximal end;
  a piston mounted in said cavity;
  means for sealingly and slidingly engaging said piston within the cavity;
  means for biasing said piston relative to said cavity and away from said proximal end;
  means for urging said piston against the biasing means and toward the proximal end;
  an elongate cannula with an elongate inner bore;
  means for securing said cannula to said piston;
  means for communicating said inner bore of said cannula with a portion of said cavity between said proximal end and said piston such that as the biasing means moves the piston away from the proximal end a vacuum is formed inside said cavity between the proximal end and the piston and such that the vacuum is communicated to the inner passage of said cannula;
a stylet positioned in said inner bore of said cannula; and
said cannula being extended out beyond a tip of said stylet in response to said biasing means in order to create a tissue collection space.

6. The instrument of claim 5 wherein:
said biasing means can bias said piston to an uncocked position;
said urging means can urge said piston against said biasing means to a cocked position; and
means for selectively locking said piston in said cocked piston.

7. The instrument of claim 5 wherein:
the volume defined by said cavity of said body is substantially larger than the volume defined by the inner passage of said cannula.

8. The instrument of claim 5 including:
means for securing said stylet to said body, such that said stylet is secured to the proximal end of said cavity.

9. The instrument of claim 5 wherein:
said stylet has a tip with a first diameter which is substantially the diameter of the bore of the cannula; and
said stylet has a shank located behind said tip, which shank has a second diameter which is less than the first diameter of the tip and which second diameter extends from the tip substantially the length of the stylet.

10. The automatic biopsy instrument including:
a body;
a cannula extending from said body, which cannula defines an inner bore;
a stylet positioned in said inner bore of said cannula;
means for biasing said cannula past a tip of said stylet in a rapid manner in order to collect a tissue sample in said inner bore of said cannula;
means provided in said body for creating a vacuum as said cannula is urged past said stylet; and
means for communicating said inner bore with the vacuum created in said body.

11. The instrument of claim 10 wherein:
said means for creating a vacuum defines a cavity and wherein a volume of said cavity is substantially larger than a volume of said inner passage and said cannula.

12. The instrument of claim 10 including:
means for securing said stylet to said body.

13. The instrument of claim 10 wherein:
said stylet has a tip with a first diameter which is substantially the diameter of the bore of the cannula; and
said stylet has a shank located behind said tip, which shank has a second diameter which is less than the first diameter of the tip and which second diameter extends from the tip substantially the length of the stylet.

14. An automatic biopsy instrument for obtaining a sample of tissue including:
a body;
a cavity defined in said body;
a piston mounted in said cavity;
an elongate cannula with an elongate inner bore;
means for communicating said inner bore of said cannula with the cavity of said body;
a stylet positioned in said inner bore of said cannula; and
means for driving the cannula out beyond said stylet into the tissue to be sampled so as to create a vacuum in said cavity and thereby assist in retaining the sample in the cannula.

15. An automatic biopsy instrument including:
a body;
a cavity defined in said body;
a piston mounted in said cavity;
means for biasing said piston relative to said cavity;
means for urging said piston against the biasing means;
an elongate cannula with an elongate inner bore;
means for securing said cannula to said piston;
means for communicating said inner bore of said cannula with the cavity of said body;
said cannula having a distal end;
a stylet with a tip, said stylet positioned in said inner bore of said cannula;
wherein said urging means can urge said piston against said biasing means to a cocked position, such that said tip of said stylet is extended from said distal end of said cannula; and
wherein said biasing means can bias said piston to an uncocked position wherein said distal end of said cannula is urged over and past said tip of said stylet in order to create a tissue collection space between the tip of the stylet and the portion of the inner bore of the cannula urged past said tip.

16. An automatic biopsy instrument including:
a body;
a cavity defined in said body and having a proximal end;
a piston mounted in said cavity;
means for sealingly and slidingly engaging said piston within the cavity;
means for biasing said piston relative to said cavity and away from said proximal end;
means for urging said piston against the biasing means and toward the proximal end;
an elongate cannula with an elongate inner bore;
means for securing said cannula to said piston;
means for communicating said inner bore of said cannula with a portion of said cavity between said proximal end and said piston such that as the biasing means moves the piston away from the proximal end a vacuum is formed inside said cavity between the proximal end and the piston and such that the vacuum is communicated to the inner passage of said cannula;
said cannula having a distal end;
a stylet with a tip, said stylet positioned in said inner bore of said cannula;
wherein said urging means can urge said piston against said biasing means to a cocked position, such that said tip of said stylet is extended from said distal end of said cannula; and
wherein said biasing means can bias said piston to an uncocked position wherein said distal end of said cannula is urged over and past said tip of said stylet in order to create a tissue collection space in the cannula inner bore between the tip of the stylet and the distal end of the cannula.

17. A needle set for an automatic biopsy instrument comprising:

a stylet;

a hollow cannula;

said stylet sized in order to be able (1) to fit inside of the hollow cannula, (2) to allow relative motion between said cannula and stylet so that relative to the hollow cannula the stylet has a first position extending from the cannula and a second position which is withdrawn inside of the hollow cannula in order to define a collection space, and (3) to allow vacuum to communicate between the stylet and the cannula to the collection space to assist in the holding of a tissue sample in the collection space;

means adapted for securing said hollow cannula to a cannula piston of the automatic biopsy instrument;

means adapted for securing the stylet to the automatic biopsy instrument so that under the urging of the automatic biopsy instrument the cannula can move from a cocked position with the stylet extending from the cannula to an uncocked position with the cannula at rest and extended past the stylet in order to define a collection space for capturing tissue.

18. The needle set in accordance with claim 17 further including:

said cannula having an inner diameter;

said stylet having a tip which has a diameter which is substantially the size of the inner diameter of said cannula, and a shaft extending behind said tip for substantially the length of the stylet, which shaft has a diameter which is less than the diameter of the said tip.

* * * * *